(12) United States Patent
Koseoglu et al.

(10) Patent No.: US 10,384,197 B2
(45) Date of Patent: Aug. 20, 2019

(54) ADDITIVES FOR GAS PHASE OXIDATIVE DESULFURIZATION CATALYSTS

(71) Applicants: SAUDI ARABIAN OIL COMPANY, Dhahran (SA); BORESKOV INSTITUTE OF CATALYSIS, Novosibirsk (RU)

(72) Inventors: Omer Refa Koseoglu, Dhahran (SA); Yaming Jin, Dhahran (SA); Zinfer Ismagilov, Novosibirsk (RU); Svetlana Yashnik, Novosibirsk (RU); Mikhail Kerzhentsev, Novosibirsk (RU); Valentin Parmon, Novosibirsk (RU)

(73) Assignees: SAUDI ARABIAN OIL COMPANY, Dhahran (SA); BORESKOV INSTITUTE OF CATALYSIS, Novosibirsk (RU)

( * ) Notice: Subject to any disclaimer, the term of this patent is extended or adjusted under 35 U.S.C. 154(b) by 46 days.

(21) Appl. No.: 15/219,749

(22) Filed: Jul. 26, 2016

(65) Prior Publication Data

US 2018/0029023 A1 Feb. 1, 2018

(51) Int. Cl.

| | | |
|---|---|---|
| *B01J 29/40* | (2006.01) | |
| *B01J 23/80* | (2006.01) | |
| *B01J 23/28* | (2006.01) | |
| *C10G 29/16* | (2006.01) | |
| *B01J 35/02* | (2006.01) | |
| *B01J 35/08* | (2006.01) | |
| *B01J 35/10* | (2006.01) | |
| *C07C 7/148* | (2006.01) | |
| *B01J 23/00* | (2006.01) | |
| *B01J 35/00* | (2006.01) | |
| *B01J 23/72* | (2006.01) | |
| *B01J 29/16* | (2006.01) | |
| *B01J 29/26* | (2006.01) | |
| *B01J 29/46* | (2006.01) | |
| *C10G 27/00* | (2006.01) | |
| *B01J 37/03* | (2006.01) | |
| *B01J 37/04* | (2006.01) | |
| *B01J 23/06* | (2006.01) | |
| *B01D 53/86* | (2006.01) | |

(52) U.S. Cl.
CPC ........... *B01J 29/405* (2013.01); *B01J 23/005* (2013.01); *B01J 23/28* (2013.01); *B01J 23/72* (2013.01); *B01J 23/80* (2013.01); *B01J 29/166* (2013.01); *B01J 29/26* (2013.01); *B01J 29/46* (2013.01); *B01J 35/0006* (2013.01); *B01J 35/026* (2013.01); *B01J 35/08* (2013.01); *B01J 35/1014* (2013.01); *B01J 35/1038* (2013.01); *B01J 35/1042* (2013.01); *C07C 7/1485* (2013.01); *C10G 27/00* (2013.01); *C10G 29/16* (2013.01); *B01D 53/8603* (2013.01); *B01D 2253/1124* (2013.01); *B01D 2255/2092* (2013.01); *B01D 2255/20761* (2013.01); *B01D 2255/20769* (2013.01); *B01D 2255/20792* (2013.01); *B01D 2255/405* (2013.01); *B01D 2255/50* (2013.01); *B01D 2255/504* (2013.01); *B01D 2255/9202* (2013.01); *B01D 2255/9207* (2013.01); *B01J 23/06* (2013.01); *B01J 35/023* (2013.01); *B01J 35/1061* (2013.01); *B01J 37/031* (2013.01); *B01J 37/04* (2013.01); *B01J 2229/183* (2013.01); *B01J 2523/00* (2013.01); *B01J 2523/17* (2013.01); *C10G 2300/1037* (2013.01); *C10G 2300/1055* (2013.01); *C10G 2300/202* (2013.01)

(58) Field of Classification Search
CPC ..................................................... B01J 29/405
See application file for complete search history.

(56) References Cited

U.S. PATENT DOCUMENTS

| | | | |
|---|---|---|---|
| 3,875,290 A | 4/1975 | Gring | |
| 3,948,760 A | 4/1976 | Gring | |
| 4,346,067 A | 8/1982 | Wachter | |
| 4,405,443 A | 9/1983 | Bertolacini et al. | |
| 4,673,557 A | 6/1987 | Nieskens et al. | |
| 5,580,534 A * | 12/1996 | Hartweg | B01J 23/005 |
| | | | 423/213.2 |
| 6,579,347 B1 | 6/2003 | Wakita et al. | |
| 7,749,346 B1 | 7/2010 | Truong | |
| 2005/0150819 A1* | 7/2005 | Wachs | C07C 7/14816 |
| | | | 208/208 R |
| 2006/0226049 A1* | 10/2006 | Nemeth | B01J 8/0438 |
| | | | 208/208 R |
| 2009/0272675 A1 | 11/2009 | Anfang et al. | |
| 2009/0281365 A1* | 11/2009 | Hatscher | B01D 53/02 |
| | | | 585/824 |
| 2010/0037774 A1 | 2/2010 | Nielsen et al. | |
| 2012/0018352 A1* | 1/2012 | Seki | B01J 21/12 |
| | | | 208/265 |
| 2013/0026072 A1 | 1/2013 | Bourane et al. | |

(Continued)

FOREIGN PATENT DOCUMENTS

WO 94/14525 7/1994

OTHER PUBLICATIONS

Performance evaluation of "ship-in-the-bottle type" heteropoly acid encaged Y-type zeolite as catalyst for oxidative desulfurization. Han Wang and Rui Wang Collect. Czech. Chem. Commun., vol. 76, No. 12, pp. 1595-1605 (Year: 2011).*

(Continued)

Primary Examiner — Douglas B Call
(74) Attorney, Agent, or Firm — Abelman, Frayne & Schwab

(57) ABSTRACT

A composition useful in oxidative desulfurization of gaseous hydrocarbons is described. It comprises a CuZnAl—O mixed oxide, and an H form of a zeolite. The mixed oxide can contain one or more metal oxide promoters. The H form of the zeolite can be desilicated, and can also contain one or more transition metals.

18 Claims, 1 Drawing Sheet

(56) References Cited

U.S. PATENT DOCUMENTS

| | | |
|---|---|---|
| 2013/0028822 A1 | 1/2013 | Bourane et al. |
| 2014/0197074 A1* | 7/2014 | Bourane ................ B01J 23/005 208/211 |
| 2017/0190641 A1 | 7/2017 | Koseoglu et al. |

OTHER PUBLICATIONS

New Gas-Phase Catalytic Oxidative Processes for Desulfurization of Diesel Fuel Z.R. Ismagilov et al. EurasianChemico-Technological Journal, vol. 17, pp. 119-128 (Year: 2015).*

Mechanochemical approach for preparation of Mo-containing beta-zeolite N.G. Kostova et al. J Physics and Chemistry of Solids, vol. 68, pp. 1169-1172 (Year: 2007).*

International Search Report and the Written Opinion of PCT/US2017/043684 dated Nov. 6, 2017.

* cited by examiner

ADDITIVES FOR GAS PHASE OXIDATIVE DESULFURIZATION CATALYSTS

FIELD OF THE INVENTION

The invention relates to catalytic compositions useful in the oxidative desulfurization of gaseous, sulfur containing hydrocarbons. More particularly, it relates to catalysts referred to as "CuZnAl" catalysts hereafter, combined with H-forms of zeolites, to form the catalytic compositions.

BACKGROUND AND PRIOR ART

Oxidative desulfurization of sulfur containing hydrocarbon fuels is a well developed field. See, e.g., pending U.S. patent application Ser. No. 14/987,141, filed Jan. 4, 2016, as well as published U.S. Patent Applications 2013/0028822 and 2013/0026072, all of which are incorporated by reference in their entirety. These materials disclose, inter alia, catalytic compositions which contain 10-50 wt % copper oxide, 5—less than 20 wt % of zinc oxide, and 20-70 wt % aluminum oxide, with X-ray amorphous phases (described infra), having formula $Cu_xZn_{1-x}Al_2O_4$, where X ranges from 0 to 1, and which also contain crystalline ZnO and CuO. These catalysts may be "doped" with one or more promoters, preferably a Group VIB metal oxide such as an oxide of Mo, W, Si, B or P. The promoter may be present in an amount up to 20 wt % of the composition.

These catalytic compositions as well as the compositions of the invention are effective catalysts for selectively oxidizing the organic sulfur compounds in gaseous hydrocarbons preferably at temperatures above 300° C.

Research in the field has shown, however, that catalytic oxidative desulfurization does not perform at a satisfactory level, when prior art catalysts are used by themselves. Hence there is interest in combining catalysts with additives to make them more effective at oxidative desulfurization. One approach is to use zeolites in combination with catalysts. In this respect see, e.g., U.S. Pat. Nos. 4,673,557; 6,579,347; 4,405,443; and 7,749,376, U.S. Patent Publications 2010/0037774 and 2007/0131589, and PCT/NL93/00282, all of which are incorporated by reference in their entirety.

None of these references, however, disclose H-forms of zeolites in combination with catalysts of the type described supra. Such forms of zeolites are disclosed, e.g., by U.S. Pat. Nos. 3,875,290; 3,948,760; and 4,346,067, all of which are incorporated by reference.

SUMMARY OF THE INVENTION

The invention relates to a catalytic composition comprising an oxidative desulfurization catalyst combined with an H-form zeolite as additive. Exemplary, but not limitative, of such H-form zeolites are HZSM-5, HY, HX, H-mordenite, H-β, and other zeolite topologies such as MFI, FAU, BEA, MOR, FER in their H-forms, as well as their desilicated forms. The zeolite portion of the catalytic composition is optionally substituted with one or more transition metals. Also, a feature of the invention are processes for manufacturing these catalysts, as well as their use in oxidatively desulfurizing gaseous, sulfur containing hydrocarbons.

The detailed description of preferred embodiments which follows elaborates upon various embodiments of the invention.

DETAILED DESCRIPTION OF PREFERRED EMBODIMENTS

Example 1

Figure 1:
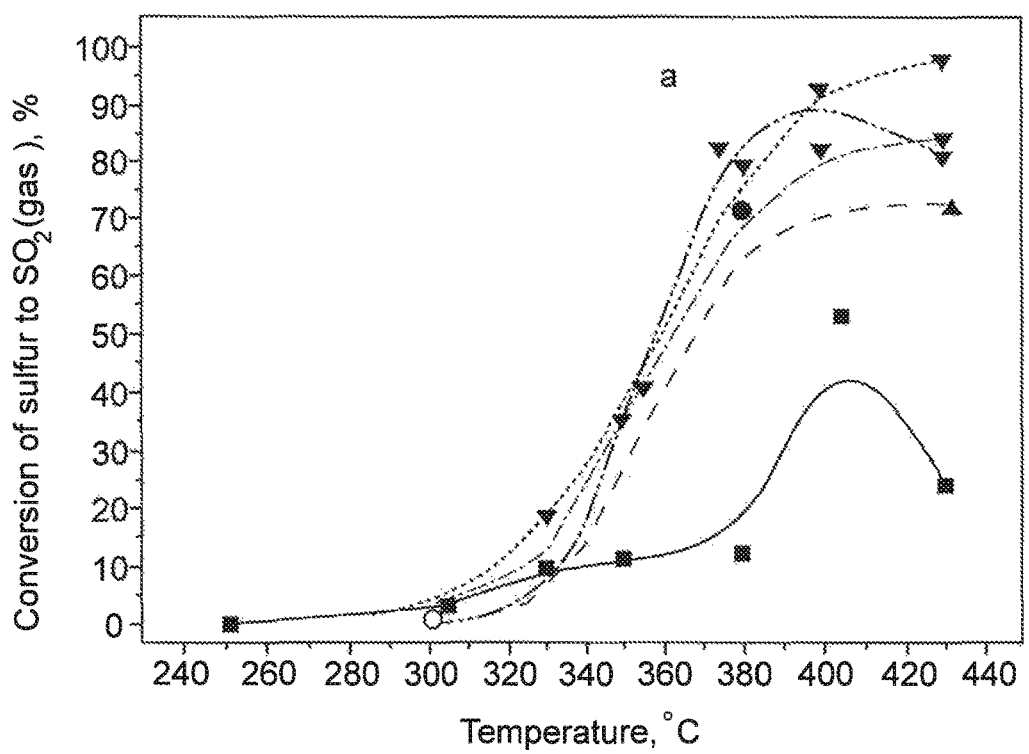
FIG. 1 shows results from tests of various catalysts in accordance with the invention. The tests involve measuring sulfur removal, and conversion of S to $SO_2$, using a test sample of DBT in toluene.

CuZnAl oxide compositions were synthesized by the precipitation method described, e.g., in Published U.S. Patent Application 2013/0026072, incorporated by reference in its entirety.

In brief, $Cu(NO_3)_2$, (0.2 moles), $Zn(NO_3)_2$ (0.07 moles), and $Al(NO_3)_3$ (0.235 moles), were dissolved in 500 ml of distilled water, to form what shall be referred to as "solution A" hereafter. The pH of the solution was 2.3.

Similarly, 19.08 g of $Na_2CO_3$, (0.18 moles), and 48 g of NaOH (1.2 moles), were dissolved in 600 ml of distilled water, to produce "solution B," which had a pH of 13.

Solution A was heated to 65° C. and solution B was added to solution A, at a rate of about 5 ml/minute, with constant agitation, until all of solution B was added. The resulting mixture had a pH of 11.0. A precipitate resulted which was aged, for 6 hours, at 65° C., pH 11. The solution was cooled to room temperature and filtered with a Buchner funnel. Precipitate was repeatedly washed with distilled water. Analysis showed that nearly all of the Cu, Zn, and Al precipitated out of the solution (99%) until PH neutral.

The precipitate was then dried at room temperature, for 12 hours, at 110° C., calcined at 500° C. for 4 hours, and ground to a fine powder.

Example 2

The composition prepared in Example 1 was then treated to incorporate molybdenum oxide ($MoO_3$), therein, via the well known incipient wetness method. To elaborate, the dried CuZnAl composition prepared in Example 1 was placed into an impregnating drum, and an impregnating solution containing $(NH_4)_6Mo_7O_{24}$ (0.22 mol/L) and $H_3BO_3$ (0.5 mol/L) was fed into the drum during its rotation. The volume of the solution was calculated from the water capacity of CuZnAl composition, and increased by 10%. The impregnated sample was left in the rotating drum for 20-30 minutes more to distribute the moisture throughout the sample evenly.

The sample was then dried at 110° C. for 12 hours and further calcined at 500° C. for 4 hours.

The dried material was dark brown in color. The calcined product contained 34-37 W % of elemental Cu, 14-14.8 W % of elemental Zn, 12-13.5 W % of elemental Al, 3-8 W % of elemental Mo, 0.4-1.5 W % of elemental % B, and 0.08-0.14 W % of elemental Na. (In all of the examples which follow, weight percent is given in terms of the pure element, rather than the oxide). The atomic ratio of the components Cu:Zn:Al was (2.5-3):1:(2.5-3). The modified catalyst had a specific surface area of 35-70 m$^2$/g, a pore volume of 0.15-0.35 cm$^3$/g and prevailing pore diameter equal to 10-20 nm.

The sample contained traces of highly dispersed CuO, ZnO, and $MoO_3$ with an X-ray amorphous oxide phase. "X-ray amorphous oxide phase" as used herein means that, when observed via high resolution transmission electron microscopy ("HRTEM"), crystalline particles ranging from 2-10 nm, and usually 2-5 nm, were observed. Lattice parameters (7.896 Å) were very close to those of spinels, hence the chemical composition, deduced from EDX data, is $Cu_{0.3}Zn_{0.7}Al_2O_4$.

The properties of CuZnAl compositions modified by oxides of molybdenum and boron are given in Table 1.

Catalytic compositions can be granulated by any known method. They can also be subjected to extrusion or tabletting by, e.g., pressing.

TABLE 1

Main characteristics of CuZnAl compositions modified by Mo and B

| | | Preparation conditions | | Chemical | | Textural properties $N_2$ desorption isotherm | | |
|---|---|---|---|---|---|---|---|---|
| # | Name | Method | Calcination temperature, °C. | composition, AAS-ICP data, wt. % | XRD composition | $S_{BET}$, $m^2/g$ | $V_\Sigma(N_2)$ $cm^3/g$ | $D_{BJH}$, nm |
| 1a | 0.5B—10MoO$_3$/ Cu—Zn—Al$_2$O$_3$ | Incipient wetness Impregnation of CuZnAl composition by $(NH_4)_6Mo_7O_{24}$ + $H_3BO_3$ solution | 500 | Cu-37.4, Zn-14.1, Al-11.9, Na-0.08, 6.9% Mo, 0.44% B $Na_{0.017}Cu_{2.69}Zn_1Al_{2.0}$ | high dispersed s.s. spinel structures (Cu, Zn)Al$_2$O$_4$, a = 7.896 Å CuO (5-661), main phase MoO$_3$ (35-609), trace | 67 | 0.19 | 11.4 |
| 1b | 0.5B—10MoO$_3$/ Cu—Zn—Al$_2$O$_3$ | Incipient wetness Impregnation of CuZnAl composition by $(NH_4)_6Mo_7O_{24}$ + $H_3BO_3$ solution | 500 | Cu-34.6, Zn-14.8, Al-13.5, Na-0.14, 6.72% Mo, 0.48% B $Na_{0.027}Cu_{2.37}Zn_1Al_{2.2}$ | high dispersed s.s. spinel structures (Cu, Zn)Al$_2$O$_4$, a = 7.896 Å CuO (5-661), main phase MoO$_3$ (35-609), trace | 69 | 0.19 | 11.1 |

Example 3

This example describes the preparation of a zeolite additive.

A commercial batch of ZSM-5 zeolite in H form with a silicate module (Si/Al atomic ratio) equal to 30 was used as a zeolite additive to the catalyst compositions described in the prior examples. The properties of the zeolite are given in Table 2, together with properties of other representative zeolites. "La" and "Y" refer to transition metals Lanthanum and Yttrium, while "DeSi" means the zeolite is in desilicated form. The silicate module can be varied in the range 15-90 W %. All of these compositions are described infra.

TABLE 2

Main characteristics of additives

| | | Chemical composition[1], wt. % | | | | | | | Si/Al atom. | Modifying additive, wt. % | Textural properties[2] | | | |
|---|---|---|---|---|---|---|---|---|---|---|---|---|---|---|
| # | Zeolite Structure | Al | Si | K | Na | Mg | Ca | Fe | | | $S_{BET}$, $m^2/g$ | $S_t$, $m^2/g$ | $V_\Sigma$, $cm^3/g$ | $V_\mu$, $cm^3/g$ |
| 1 | H-ZSM-5-30 | 1.43 | 42.89 | 0.01 | 0.06 | 0.03 | 0.04 | 0.65 | 30 | — | 450 | 28 | 0.255 | 0.125 |
| 2 | La/H-ZSM-5-30 | 1.43 | 42.89 | 0.01 | 0.06 | 0.03 | 0.04 | 0.65 | 30 | 4.75 | 444 | 52 | 0.22 | 0.12 |
| 3 | Y/H-ZSM-5-30 | 1.43 | 42.89 | 0.01 | 0.06 | 0.03 | 0.04 | 0.65 | 30 | 4.26 | 440 | 48 | 0.21 | 0.12 |
| 4 | H-DeSi-ZSM5-(30) | 1.84 | 40.2 | 0.01 | 0.01 | 0.01 | 0.01 | 0.65 | 21 | — | 618 | 300 | 0.52 | 0.11 |
| 5 | H-Y | 11.6 | 27.3 | 0.1 | 0.15 | 0.00 | 0.44 | 0.44 | 2.2 | — | 1087 | 1080 | 0.60 | 0.38 |

[1]data of elemental analysis: X-ray fluorescence analysis (samples 1-4) and AAC-ICP (samples 5-7)
[2]determined from nitrogen sorption isotherms, here $S_{BET}$ - BET surface area (calculated at P/P$_0$ from 0.05 to 0.20), $S_t$ - external surface area of crystallite (calculated from t-plot, t-value were between 0.6 and 1.0 nm after t approximate as 5.27 * [(-1.000/ln(P/Po))]$^{0.331}$); $V_\Sigma$ - mesopore volume, calculated from nitrogen sorption isotherm at P/Po close to 1; and $V_\mu$ - micropore volume, determined from t-plot analysis;

Example 4

The CuZnAl composition of example 2 and the ZSM-5 of Example 3 were weighed and mixed at a weight proportion 85% to 15%. The mixture was thoroughly ground for 10 minutes, pressed and fractionized, without thermal treatment.

Major physicochemical properties of the obtained material are given in Table 3, together with the physicochemical properties of other compositions described herein.

TABLE 3

Textural properties of modified 0.5B—10MoO$_2$/Cu—Zn—Al$_2$O$_3$ (B—Mo/CuZnAl) catalysts (85 W %) with additives (15 W %)

| | | Textural properties, $N_2$ desorption isotherm | | |
|---|---|---|---|---|
| # | Additive/Catalyst[1] | $S_{BET}$, $m^2/g$ | $V_\Sigma(N_2)$ $cm^3/g$ | $D_{BJH}$, nm |
| 1 | Additive: H-ZSM-5 + Catalyst: B—Mo/CuZnAl | 85.5 | 0.19 | 18.6 |
| 2 | Additive: La/ZSM-5 + Catalyst: B—Mo/CuZnAl | 76 | 0.15 | 16.3 |
| 3 | Additive: Y/ZSM-5 + Catalyst: B—Mo/CuZnAl | 76 | 0.15 | 17.0 |

TABLE 3-continued

Textural properties of modified 0.5B—10MoO$_2$/Cu—Zn—Al$_2$O$_3$ (B—Mo/CuZnAl)
catalysts (85 W %) with additives (15 W %)

| | | Textural properties, N$_2$ desorption isotherm | | |
|---|---|---|---|---|
| # | Additive/Catalyst[1] | S$_{BET}$, m$^2$/g | V$_\Sigma$(N$_2$) cm$^3$/g | D$_{BJH}$, nm |
| 4 | Additive: DeSi-ZSM-5(Si/Al = 30) + Catalyst: B—Mo/CuZnAl | 85 | 0.17 | 14.1 |
| 5 | Additive: H—Y + Catalyst: B—Mo/CuZnAl | 84 | 0.19 | 10.5 |
| 6 | Additive: Na-DeSi-Y + Catalyst: B—Mo/CuZnAl | 82 | 0.21 | 10.4 |
| 7 | Additive: H-DeSi-Y + Catalyst: B—Mo/CuZnAl | 73 | 0.19 | 10.5 |

[1]All catalysts were prepared by physical mixing of additive (15%) with 85% B—Mo/CuZnAl catalyst), prepared by pressing 3 times, with subsequent calcination at 500° C. Chemical and XRD-phase properties of B—Mo/CuZnAl and additives are presented in Table 1 and 2, respectively

Example 5

This example describes preparation of a CuZnAl composition modified by MoO$_3$, B, and a zeolite additive containing La: 0.5B-10MoO$_3$/Cu—Zn—Al$_2$O$_3$+15% La/H-ZSM-5

The composition was prepared in the same manner as the composition of Example 4 with the only difference being that the composition of the zeolite additive, i.e., it was a zeolite with ZSM-5 structure, modified by lanthanum (La/H-ZSM-5). La and Y can be introduced in ZSM-5 by known routes other than those used herein, such as via ion-exchange mode using an aqueous solution of La and Y salts. La and Y content can vary within the range 0.1 to 5 W %.

For the synthesis of this zeolite additive, an H-ZSM-5 sample in H form with a silicate module equal to 30 as described supra was subjected to incipient wetness impregnation with an aqueous solution of lanthanum nitrate La(NO$_3$)$_3$. The volume of the solution taken for the impregnation was calculated from water capacity of the zeolite powder (VH$_2$O=0.6 ml/g) increased by 10%. The concentration of La(NO$_3$)$_3$ in the solution was 0.65 mol/L.

The sample was then dried for 4 hours at 110° C. and calcined for 4 h at 500° C.

The content of lanthanum in La/H-ZSM-5 was 4.75 wt. %. Some of its properties are presented in Table 2, supra.

The composition and some properties of CuZnAl catalyst modified by Mo, B and La/H ZSM-5 are given in Table 3, supra.

Example 6

This example describes a preparation of a CuZnAl composition modified by MoO$_3$, B and zeolite additive containing Y: 0.5B-10MoO$_3$/Cu—Zn—Al$_2$O$_3$+15Y % La/H-ZSM-5. La and Y can be introduced in ZSM-5 by routes other than those used herein, such as ion-exchange using an aqueous solution of an La or Y salt. La and Y content can vary within 0.1 to 5 W %.

The preparation method used followed example 4, supra, but used a zeolite with ZSM-5 structure, modified by yttrium (Y/H-ZSM-5).

For the synthesis of Y/H-ZSM-5, a ZSM-5 sample in H form with a silicate module equal to 30 as described supra was subjected to incipient wetness impregnation by an aqueous solution of yttrium nitrate Y(NO$_3$)$_3$. The volume of the solution taken for the impregnation was calculated from the water capacity of the zeolite powder (VH$_2$O=0.6 ml/g) increased by 10%. The concentration of Y(NO$_3$)$_3$ in the solution was 1 mol/L.

The sample was then dried for 4 hours at 110° C. and calcined for 4 h at 500° C.

The content of yttrium in Y/H-ZSM-5 was 4.75 wt. %. Its main properties are presented in Table 2, supra.

The composition and main properties of CuZnAl catalyst modified by Mo, B and Y/H ZSM-5 are given in Table 3, supra.

Example 7

Preparation of CuZnAl composition modified by MoO$_3$, B and desilicized ZSM-5 structure (H-DeSi-ZSM-5)-0.5B-10MoO$_2$/Cu—Zn—Al$_2$O$_3$+15% H-DeSi-ZSM-5 is described.

Again, preparation followed example 4, but used a desilicized ZSM-5 structure (H-DeSi-ZSM-5).

For the synthesis of H-DeSi-ZSM-5 a commercially available H-ZSM-5 sample in H form with a silicate module equal to 30 was placed into a reactor with a water jacket and subjected to desilicization in 0.2M NaOH solution at 80° C. for 2 h. The ratio of the mass of zeolite (g) to the volume of the solution (ml) was equal to 30. Then the sample was filtered, and washed with a 5 fold volume of water.

After washing, sodium cations were removed from the sample by an ion-exchange procedure with 0.5M NH$_4$NO$_3$ at 60° C. for 1 hour. The ratio of the mass of desilicated zeolite (g) to the volume of the solution (ml) was equal to 30. Then the sample was filtered and washed by water to attain neutral pH of the washing water.

The obtained material was dried at 110° C. for 4 h and calcined at 500° C. for 4 h.

Main properties of H-DeSi-ZSM-5 are presented in Table 2, supra.

The composition and main properties of CuZnAl catalyst modified by Mo, B and H-DeSi-ZSM-5 are given in Table 3, supra.

Example 8

The preparation of a CuZnAl composition modified by MoO$_3$, B and desilicized Na—Y structure (Na-DeSi-Y).-0.5B-10MoO$_3$/Cu—Zn—Al$_2$O$_3$+15% is described herein.

Again, Example 4 was followed using a desilicized zeolite with H—Y structure.

The conditions of the preparation of the desilicized zeolite with H—Y structure were similar to those for the preparation of the desilicized zeolite with HZSM-5 structure. After treatment with NaOH, the sample was designated as Na-DeSi-Y and it was not further subjected to ion-exchange. Properties of the desilicated zeolite additive, Na-DeSi-Y and CuZnAl catalyst modified by additions of Mo, B and Na-DeSi-Y are given in Table 2 and 3, supra.

Example 9

This example describes preparation of a CuZnAl composition modified by $MoO_3$, B and desilicized zeolite with H—Y structure (H-DeSi-Y).-0.5B-10$MoO_2$/Cu—Zn—$Al_2O_3$+15%

Again, Example 4 was followed using a desilicized zeolite with H—Y structure. The base zeolite is commercially available.

The conditions of the preparation of the desilicized zeolite with H—Y structure were similar to those for the preparation of the desilicized zeolite with HZSM-5 structure. After treatment with NaOH, the sample was subjected to ion-exchange with a solution of ammonium nitrate. The product was designated as H-DeSi-Y.

Properties of the desilicated zeolite additive H-DeSi-Y and CuZnAl catalyst modified by additions of Mo, B and H-DeSi-Y are given in Table 2 and 3, supra.

Example 10

Catalytic compositions prepared in accordance with the invention were tested to determine their ability to oxidatively desulphurize hydrocarbons. In this example, DBT was dissolved in toluene, to produce a test mixture containing 1% sulphur. Catalytic compositions as described supra, viz:
0.5B+10 Mo/CuZnAl
ZSM-5/0.5B+10 Mo/CuZnAl
La-ZSM-5/0.5B+10 Mo/CuZnAl
Y-ZSM-5/0.5B+10 Mo/CuZnAl
DeSi-ZSM-/0.5B+10 Mo/CuZnAl
NaDeSi-Y/0.5B+10 Mo/CuZnAl
HDeSi-Y/0.5B+10 Mo/CuZnAl
were tested.

In the tests, the test mixture described herein was combined with each of the catalytic compositions listed, and heated. The conversion of sulfur to $SO_2$, and the percentage of sulfur removal were measured, and are depicted in FIG. 1. At the temperatures tested (240-440° C.), the test mixture was in gaseous phase.

Review of these figures show that maximum catalytic activity was significantly higher when the zeolites were used, than not.

Example 11

The catalytic compositions described supra were then tested for their ability to catalyze the oxidative desulfurization of residual fuel oil. The properties of the test material (residual fuel oil) were:

| | |
|---|---|
| Density: | 0.96 g/cc |
| Carbon (wt %) | 86.0 |
| Hydrogen (wt %) | 9.25 |
| Sulphur (wt %) | 2.6 |
| Nitrogen (ppmw) | 5.800 |
| MCR (wt %) | 6.0 |
| Boiling Point: | 370° C. or greater |

The conditions used for the test are presented in Table 4 which is set forth infra. Note the increase in desulfurization using the compositions of the invention, as compared to the prior art (56.6 versus 37.1).

TABLE 4

Results of study of ODS reaction with residual fuel oil on CuZnAl catalyst modified by B, Mo and catalyst modified by B, Mo and Y-zeolite

| Catalyst | Additive | Temp. ° C. | Feed S W % | $O_2$/S | GHSV $h^{-1}$ | WHSV $h^{-1}$ | $CO_2$ V % | $SO_2$ V % | $H_2S$ V % | COS V % | DSLP[1] W % |
|---|---|---|---|---|---|---|---|---|---|---|---|
| 1B—5$MoO_3$/CuZnAl | — | 485 | 2.6027 | 25 | 7850 | 6 | 21.812 | 0.315 | 0.006 | 0 | — |
| 1B—5$MoO_3$/CuZnAl | — | 500 | 2.6027 | 25 | 7850 | 6 | 27.021 | 0.525 | 0.016 | 0 | 46.8 |
| 0.5B—10$MoO_3$/CuZnAl | Y Zeolite | 400 | 2.6027 | 25 | 7855 | 6 | 20.903 | 0.679 | 0.001 | 0 | 57.6 |

[1]DSLP—Desulfurization based on liquid analysis, elemental sulfur in the liquid phase Example 12

Similar experiments were carried out on a blend of diesel and residual fuel. Relevant properties are:

| | |
|---|---|
| Density: | 0.906 g/cc |
| Sulfur (wt %) | 1.30 |
| MCR (wt %) | 1.8 |

Table 5, which follows, shows the conditions, and the results of the work. Note the increase in desulfurization from 57.4 to 71.1.

TABLE 5

Results of study of ODS reaction with blend on CuZnAl catalyst modified by B, Mo and catalyst modified by B, Mo and Y-zeolite

| Catalyst | Catalyst | Temp. ° C. | Feed S W % | $O_2$/S | GHSV $h^{-1}$ | WHSV $h^{-1}$ | $CO_2$ V % | $SO_2$ V % | $H_2S$ V % | COS V % | DSLP[1] W % |
|---|---|---|---|---|---|---|---|---|---|---|---|
| 0.5B + 10$MoO_3$/CuZnAl | — | 415 | 1.0882 | 25 | 7850 | 6 | 3.334 | 0.033 | 0.006 | 0 | 57.4 |
| 0.5B + 10$MoO_3$/CuZnAl | Y Zeolite | 400 | 1.452 | 30 | 7855 | 6 | 1.105 | 0.02 | 0.035 | 0 | 71.1 |

[1]DSLP—Desulfurization based on liquid analysis, elemental sulfur in the liquid phase Example 13

Figure 2:
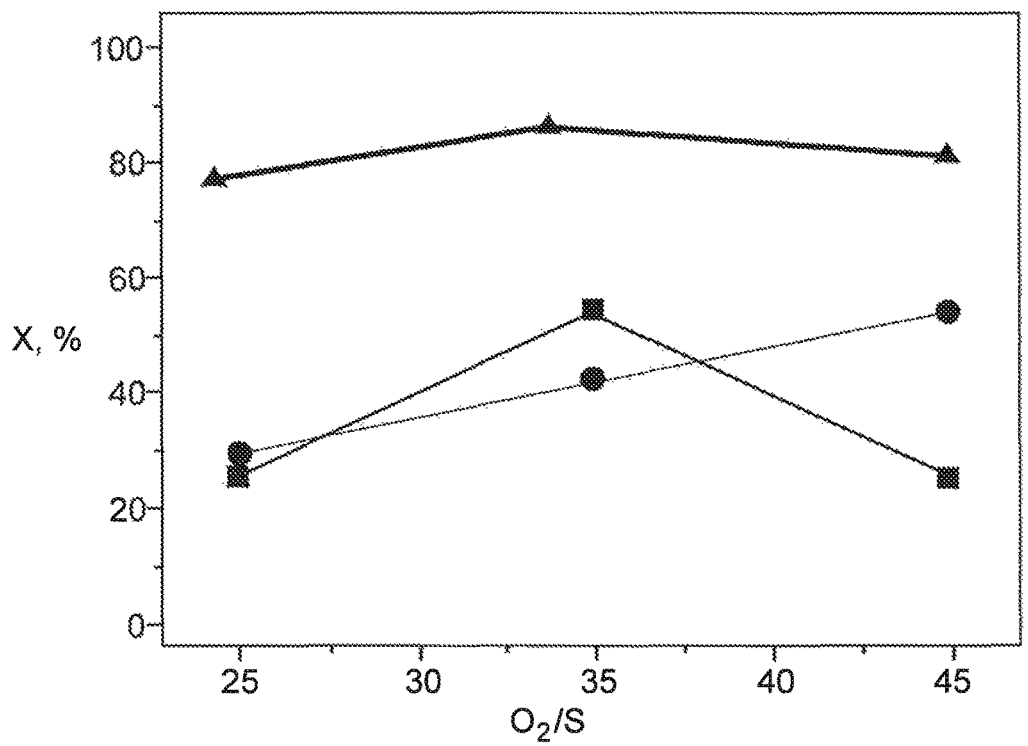
FIG. 2 shows the results of tests using a catalytic composition of the invention on diesel fuel.

The catalytic composition Y-zeolite/0.5B-10 $MoO_3$CuZn was tested for its ability to remove sulfur from diesel fuel. The test was carried out at 400° C., GHSV=7860 $h^{-1}$, WHSV h$^{-1}$. Sulfur content was 0.97 wt %. FIG. 2 shows the sulfur removal, the conversion of sulfur to SO$_2$, and oxygen consumption, at varying O$_2$/S ratios.

The foregoing disclosure sets forth features of the invention, which include a catalytic composition and its use. The catalytic composition comprises a CuZnAl—O mixed oxide, where the weight percentages of the oxides are:

10-50 CuO
5→20 ZnO
20-70 Al$_2$O$_3$

These mixed oxides also contain a highly dispersed spinel oxide phase, where this phase has formula

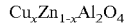

with x ranging from 0 to 1, preferably 0.1 to 0.6 and most preferably from 0.2 to 0.5. Optionally, the mixed oxide can contain at least one oxide promoter, such as one or more oxides of Mo, W, Si, B, or P.

The composition also includes at least one zeolite in H form, such as HZSM-5, HY, HX, H-mordenite, H-β, MF1, FAU, BEA, MOR, or FER. These H forms can be desilicated, and/or contain one or more transition metals, such as La or Y.

The mixed oxide component may be in granular form, and the composition as a whole may be formed, using known methods, into a cylinder, a sphere, a trilobe, a quatrolobe, or any form desired. When in granular form, the mixed oxide granules have a diameter of from 1 mm to 4 mm. The mixed oxide also preferably has a surface area of from 10 m$^2$/g to 100 m$^2$/g, preferably from 50 m$^2$/g to 100 m$^2$/g and/or a total pore volume of from about 0:1 cm$^3$/g to about 0.5 cm$^3$/g.

Referring again to the mixed oxide composition, a preferred weight distribution is:

20-45 wt %/CuO
10→20 ZnO
20-70 Al$_2$O$_3$ and even more preferably:

30-45 CuO
12→20 ZnO
20-40 Al$_2$O$_3$

The H-form zeolite can comprise from about 5 to about 50 wt % of the composition, and a silicate module of from 2 to 90.

The composition can be used to oxidatively desulfurize a gaseous hydrocarbon or hydrocarbon mixture, such as fuel oil, crude oil, diesel fuel, etc., by contacting a gaseous hydrocarbon which contains sulfur to said composition, at a temperature of, e.g., from 200° C. to 500° C., preferably from 240° C. to 440° C. Other operating parameters, such as feed, O$_2$/S ratio, GHSV, WHSV and so forth, are parameters that are set by the individual artisan.

Other features of the invention will be clear to the skilled artisan and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A method for oxidatively reducing sulfur content in a gaseous hydrocarbon feedstock comprising: contacting said gaseous hydrocarbon feedstock with a mixed oxide catalytic composition prepared by precipitation method, wherein said mixed oxide catalytic composition contains (i) copper oxide in an amount ranging from 10 weight percent (wt %) to 50 wt %, (ii) zinc oxide in an amount ranging from 5 wt % to less than 20 wt %, (iii) aluminum oxide in an amount ranging from 20 wt % to 70 wt %, and (iv) a boron oxide promoter, wherein said mixed oxide catalytic composition (a) has a spinel oxide phase with formula Cu$_x$Zn$_{1-x}$Al$_2$O$_4$ wherein x ranges from O to 1, (b) contains dispersed ZnO and CuO, and adding at least one zeolite in H form selected from the group consisting of: HZSM-5, HY, HX, H-mordenite, MFI, FAU, BEA, MOR, and FER to said mixed oxide catalytic composition, said zeolite in H form containing at least one transition metal additive, wherein oxidative reduction of sulfur is carried out at a temperature of from 240° C. to 440° C., to oxidatively desulfurize said gaseous hydrocarbon feedstock.

2. The method of claim 1, wherein said mixed oxide catalytic composition is in granular form.

3. The method of claim 1, wherein said mixed oxide catalytic composition is formed as a cylinder, a sphere, a trilobe, or a quatrolobe.

4. The method of claim 2, wherein granules of said mixed oxide catalytic composition has a diameter of from 1 mm to 4 mm.

5. The method of claim 1, wherein said mixed oxide catalytic composition has a surface area of from 10 m$^2$/g to 100 m$^2$/g.

6. The method of claim 5, wherein said mixed oxide catalytic composition has a surface area of from 50 m$^2$/g to 100 m$^2$/g.

7. The method of claim 1, wherein the total pore volume of said mixed oxide catalytic composition is from about 0.1 cm$^3$/g to about 0.5 cm$^3$/g.

8. The method of claim 1, wherein said mixed oxide catalytic composition comprises from 20 wt % to 45 wt % CuO, from 10 wt % to less than 20 wt % ZnO, and from 20 wt % to 70 wt % of Al$_2$O$_3$.

9. The method of claim 8, wherein said mixed oxide catalytic composition comprises from 30 wt % to 45 wt % CuO, from 12 wt % to less than 20 wt % ZnO, and from 20 wt % to 40 wt % Al$_2$O$_3$.

10. The method of claim 1, wherein X is from 0.1 to 0.6.

11. The method of claim 10, wherein X is from 0.2 to 0.5.

12. The method of claim 1, wherein said mixed oxide catalytic composition further comprises an oxide promoter which is an oxide of Mo, W, Si, or P.

13. The method of claim 1, wherein said at least one zeolite in H-form is desilicated.

14. The method of claim 1, wherein said transition metal additive is La or Y.

15. The method of claim 1, wherein said at least one zeolite in H-form comprises from about 5 to about 50 percent by weight of said mixed oxide catalytic composition.

16. The method of claim 1, wherein said at least one zeolite in H-form has a silicate module (silicon to aluminum atomic ratio) of from 2 to 90.

17. The method of claim 1, wherein said at least one zeolite in H-form has an amorphous or crystalline structure.

18. The method of claim 1, wherein said mixed oxide catalytic composition further comprises a Mo oxide.

* * * * *